(12) United States Patent
Chanrion et al.

(10) Patent No.: US 12,721,734 B2
(45) Date of Patent: Sep. 1, 2026

(54) COMPUTER-ASSISTED METHOD AND SYSTEM FOR PLANNING AN OSTEOTOMY PROCEDURE

(71) Applicant: KYNISKA ROBOTICS, Saint-Martin-D'Hères (FR)

(72) Inventors: Marie-Anne Chanrion, Saint-Martin-D'Hères (FR); Sylvain Fontaine, Saint-Martin-D'Hères (FR); Thomas Lonjaret, Saint-Martin-D'Hères (FR)

(73) Assignee: OSTESYS, Saint-Martin-d'Hères (FR)

(*) Notice: Subject to any disclaimer, the term of this patent is extended or adjusted under 35 U.S.C. 154(b) by 29 days.

(21) Appl. No.: 18/720,867

(22) PCT Filed: Dec. 20, 2022

(86) PCT No.: PCT/EP2022/087074
§ 371 (c)(1),
(2) Date: Jun. 17, 2024

(87) PCT Pub. No.: WO2023/118200
PCT Pub. Date: Jun. 29, 2023

(65) Prior Publication Data

US 2025/0064601 A1 Feb. 27, 2025

(30) Foreign Application Priority Data

Dec. 20, 2021 (EP) .................................... 21306855

(51) Int. Cl.
*A61F 2/46* (2006.01)
*A61B 34/10* (2016.01)
*G16H 50/50* (2018.01)

(52) U.S. Cl.
CPC .............. *A61F 2/461* (2013.01); *A61B 34/10* (2016.02); *G16H 50/50* (2018.01);
(Continued)

(58) Field of Classification Search
CPC ...................................................... A61F 2/461
See application file for complete search history.

(56) References Cited

U.S. PATENT DOCUMENTS

| | | | | |
|---|---|---|---|---|
| 6,711,432 | B1 | 3/2004 | Krause | |
| 9,770,302 | B2 * | 9/2017 | Kang | A61B 17/16 |
| 2004/0106926 | A1 * | 6/2004 | Leitner | A61B 17/152 606/87 |

OTHER PUBLICATIONS

Dessyn Edouard et al.—"Adding a protective K-wire during opening high tibial osteotomy increases lateral hinge resistance to fracture"—Knee Surgery, Sports traumatology, Arthroscopy, Springer International, Berlin, DE, vol. 28, No. 3, Feb. 19, 2019 (Feb. 19, 2019), pp. 751-758.

(Continued)

*Primary Examiner* — Andrew Yang
(74) *Attorney, Agent, or Firm* — Thomas | Horstemeyer, LLP

(57) ABSTRACT

The present disclosure relates to a computer-assisted method for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, comprising: •—obtaining an at least partial 3D model of the tibia and/or the femur and a 3D model of the implant; •—receiving at least one user input comprising at least one target alignment parameter; •—based on the at least partial 3D model of each bone and the at least one user input, implementing a dynamic simulation of each cut and of distraction or closing of the bone portions to compute a deformed model of each bone to be cut resulting from the simulated cut(s) and
(Continued)

distraction or closing; •—based on the deformed bone model(s) and the at least partial 3D model of the implant, computing an optimal placement of the implant onto the deformed bone.

21 Claims, 7 Drawing Sheets

(52) U.S. Cl.
CPC ... *A61B 2034/102* (2016.02); *A61B 2034/105* (2016.02); *A61F 2002/4633* (2013.01)

(56) References Cited

OTHER PUBLICATIONS

European Office Action received in related EP Application No. 22843215.9, mailed Jul. 31, 2025.
Carrillo Fabio et al: "An automatic genetic algorithm framework for the optimization of three-dimensional surgical plans of forearm corrective osteotomies", Medical Image Analysis, vol. 60, Feb. 1, 2020 (Feb. 1, 2020), p. 101598.
Shi Jianhui et al: "Three dimensional patient-specific printed cutting guides for closing-wedge distal femoral osteotomy", International Orthopeadics, Springer, Berlin, DE, vol. 43, No. 3, Jun. 27, 2018 (Jun. 27, 2018), pp. 619-624.
European Search Report in related EP Application No. 21306855; mailed Jun. 9, 2022.
PCT Search Report in related PCT Application No. PCT/EP2022/087074; mailed Mar. 20, 2023.

* cited by examiner

COMPUTER-ASSISTED METHOD AND SYSTEM FOR PLANNING AN OSTEOTOMY PROCEDURE

CROSS REFERENCE TO RELATED APPLICATIONS

This application is the 35 U.S.C. § 371 national stage application of PCT Application No. PCT/EP2022/087074, filed Dec. 20, 2022, which application claims the benefit of European Application No. EP 21306855.4 filed Dec. 20, 2021, both of which are hereby incorporated by reference herein in their entireties.

TECHNICAL FIELD

The present disclosure relates to a computer-assisted method and a system for planning an osteotomy procedure on a tibia and/or a femur of a patient's lower limb to correct a misalignment of said lower limb.

TECHNICAL BACKGROUND

Osteotomy is a surgical procedure used to correct a misalignment of a limb, in particular it can be performed on a lower limb (leg). To that end, an osteotomy procedure comprises cutting a part of a bone of said limb to create a bone hinge and moving the bone portions around the hinge to achieve a better alignment of the limb. Once said alignment has been achieved, an implant is placed between the bone portions and screwed onto each bone end to maintain them in said position.

Osteotomy of a lower limb is complex and requires not only a precise diagnosis of the misalignment but also an accurate control of the surgical procedure itself.

Generally, the diagnosis of a misalignment is made based on a preoperative 2D X-ray image, in particular according to a frontal view, acquired in the standing position of the patient. The surgeon analyses said X-ray image and draws lines between characteristic points to determine alignment measurements. Based on said measurements, in particular the analysis of the hip-knee-ankle (HKA) alignment, a tibial and/or femoral cut is deduced, either open or closed. An open-wedge or closed-wedge osteotomy procedure is decided by the surgeon. This osteotomy cut will allow reorienting the bone in a three-dimensional space. The cut is generally wedge-shaped, with position and dimensions that can be determined from the 2D X-ray image.

The planning of the osteotomy procedure has to take into account several constraints.

First, the bone(s) to be cut have to be defined. In some situations, only one of the tibia or the femur have to be cut. In other situations, both the tibia and the femur have to be cut.

Then, one or more cuts have to be defined in each bone to be cut. In some situations, only one cut may be necessary. In other situations, two or more cuts may be necessary to provide the suitable correction.

Each bone cut has to be planned considering the hinge zone to be preserved.

The geometry of the hinge zone has to be defined before the cut and has to resist the distraction or closing.

Besides, a misplacement of the implant can compromise the alignment goal of the osteotomy procedure. A misplacement and/or unsuitable length of the screws can compromise the hinge, the implant stability and the overall implant resistance.

At last, if during the distraction of the bone, the hinge breaks, the fixation of the bone requires at least one extra implant and/or staples. A misplacement of the implant(s) and/or staples can compromise the alignment objective of the osteotomy and may create uncontrolled limb deformation.

SUMMARY OF THE DISCLOSURE

In view of the above constraints, a goal of the invention is to define a method for planning an osteotomy that defines an optimal position and orientation of the bone cut(s) and the hinge zone and an optimal position and orientation of the implant and the screws intended to fix the implant to the bone.

To that end, the present disclosure relates to a computer-assisted method for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, comprising:

- obtaining, at a processor of a computer, an at least partial 3D model of the tibia and/or the femur and a 3D model of the implant;
- receiving, at the processor, at least one user input comprising at least one target alignment parameter;
- based on the at least partial 3D model of each bone and the at least one user input, implementing by the processor a dynamic simulation of each cut and of distraction or closing of the bone portions to compute a deformed model of each bone to be cut resulting from the simulated cut(s) an distraction or closing, said dynamic simulation comprising a simulation of the movement of the bone portions from an initial position prior to each bone cut to a final position defining the deformed configuration of the bone achieving a corrected alignment of the limb;
- based on the deformed bone model(s) and the at least partial 3D model of the implant, computing by the processor an optimal placement of the implant onto the deformed bone.

In some embodiments, the dynamic simulation comprises:

- computing by the processor at least one cutting plane defining the two bone portions and at least one hinge zone to be preserved for each bone to be cut;
- computing by the processor a distraction or closing of the two bone portions relative to each other about the hinge zone until a final position to reach the at least one target alignment parameter;
- computing by the processor the deformed bone model comprising the hinge zone and the two bone portions in said final position.

In some embodiments, the user input further comprises at least one of:

- a type of surgery procedure,
- a type of osteotomy,
- a validation of an automatic plan,
- at least one clinical parameter selected from: a hinge position, a zone not allowed to be cut, an entry point for the cut, and a cutting plane.

The at least one target alignment parameter can typically comprise: a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA), a joint line convergence angle (JLCA), a posterior tibial slope (PTS), a hip abduction angle (HAA), a tibial plafond inclination (TPI), a talar inclination angle (TIA), a lateral patellar tilt (LPT) and/or a lateral patellar shift (LPS).

In some embodiments, the osteotomy procedure comprises an open-wedge osteotomy and the dynamic simulation of the cut and distraction of the bone portions computes an osteotomy wedge extending between the two bone portions.

In other embodiments, the osteotomy procedure comprises a closed-wedge osteotomy and the dynamic simulation of the cut and closing of the bone portions computes an osteotomy wedge extending between the two bone portions.

The computation of said osteotomy wedge may comprise the computation of at least one of:

- at least one osteotomy plane according to which the bone is to be cut;
- a cut zone defined as an intersection between the 3D model of the bone and said at least one osteotomy plane;
- a tilt line defined as a border of the cut zone about which the two bone portions are to be distracted or closed;
- the hinge zone being defined as a zone on the at least one osteotomy plane in which no cut is carried out.

The method may advantageously comprise validating the osteotomy wedge by the user before computing the optimal placement of the implant.

In some embodiments, the method comprises identifying anatomical landmarks on the 3D model of the bone and taking into account said anatomical landmarks at the processor for implementing the dynamic simulation of the cut and the distraction or closing of the bone portions.

In some embodiments, the at least partial 3D model of the bone is a biomechanical model and the dynamic simulation and the computation of the optimal placement of the implant are based on said biomechanical model so as to take into account influence of soft tissues onto the deformed bone.

In some embodiments, the optimal placement of the implant is computed based on at least one of the following constraints:

- a protrusion of the implant from the bone surface is minimized;
- each screw hole of the implant is located in front of a bone surface;
- the placement of the implant is carried out according to predetermined instructions of use;
- screw orientation is optimised to maximise stress recovery;
- friction of the implant on surrounding soft tissues is minimized.

In some embodiments, the computation of the optimal placement of the implant comprises computing by the processor an optimal size and/or orientation of each screw for fixing the implant to the bone portions.

In some embodiments, the method further comprises displaying the deformed bone model and the 3D model of the implant on a user interface.

The at least partial 3D model of each bone may be obtained by at least one of the following methods:

- segmentation of a 3D image of the respective bone;
- palpation of a surface of the respective bone; and
- bone morphing.

In some embodiments, the method comprises interactively modifying by a user the deformed bone model and/or the placement of the implant.

The above-described embodiments may be combined whenever technically relevant.

Another object of the disclosure is a system for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, said system comprising at least one processor and at least one user interface coupled to the at least one processor, wherein the at least one processor is configured to:

- obtain an at least partial 3D model of the tibia and the femur and a 3D model of the implant;
- receive at least one user input via the user interface comprising at least one target alignment parameter;
- based on the at least partial 3D model of each bone and the at least one user input, implement a dynamic simulation of each cut and of distraction or closing of the bone portions to compute a deformed model of each bone to be cut resulting from the simulated cut(s) and distraction or closing, said dynamic simulation comprising a simulation of the movement of the bone portions from an initial position prior to each bone cut to a final position defining the deformed configuration of the bone achieving a corrected alignment of the limb;

based on the deformed bone model(s) and the at least partial 3D model of the implant, compute an optimal placement of the implant onto the deformed bone.

A computer-assisted osteotomy procedure may be implemented as follows:

- fixing at least two trackers to the tibia and the femur; preferably, an additional tracker is fixed to the bone to be cut, on the other side of the planned cut(s), so that at least one tracker is fixed to each bone portion generated by the planned cut(s); alternatively, a mechanical device may be used to follow the advancement of the osteotomy in real time;
- performing at least one cut to create two bone portions articulated by a hinge;
- moving the bone portions away or toward each other to reach the planned deformed configuration; and
- fixing the implant to the bone portions to maintain the bone in the deformed configuration.

The method comprises, during movement of the bone portions, determining, by the control unit, the current position and orientation of the bone portions in real time based on localization data relating to the trackers and the mechanical device (if any), and comparing in real time said current positions and orientations with theoretical positions and orientations provided by the dynamic simulation.

BRIEF DESCRIPTION OF THE DRAWINGS

Further features and advantages will become apparent from the following detailed description, based on appended drawings in which.

DETAILED DESCRIPTION OF EMBODIMENTS

The planning method is carried out automatically by a computer, based on models of the tibia and the femur and on user inputs.

The computer conventionally comprises at least one processor configured to implement algorithms to compute a surgical plan, at least one memory, and at least one user interface allowing a user to enter inputs and/or to correct the proposed surgical plan. The user interface comprises at least one display configured to display the surgical plan and, if applicable, modifications brought by the user.

The goal of the planning is to define not only the volume of bone to be distracted or removed to correct the misalignment of the patient's limb, but also the position and orientation of the implant relative to the bone in the corrected position, and, advantageously, the position and orientation of the screws to be used for fixing the implant to the bone portions.

The volume of bone to be distracted or removed may be typically computed as a volume that has a substantially wedge shape. The geometry of said volume is correlated with the correction parameters; in particular, each correction parameter can be a geometric feature of the volume, such as a length of a side of the volume or an angle between two sides or faces of the volume. Generally, it is possible to establish a relationship between angles and distances. Thus, if the volume is defined by angle values, one can also define the volume by distance (e.g. length, width, height) values, and conversely.

Figure 1:
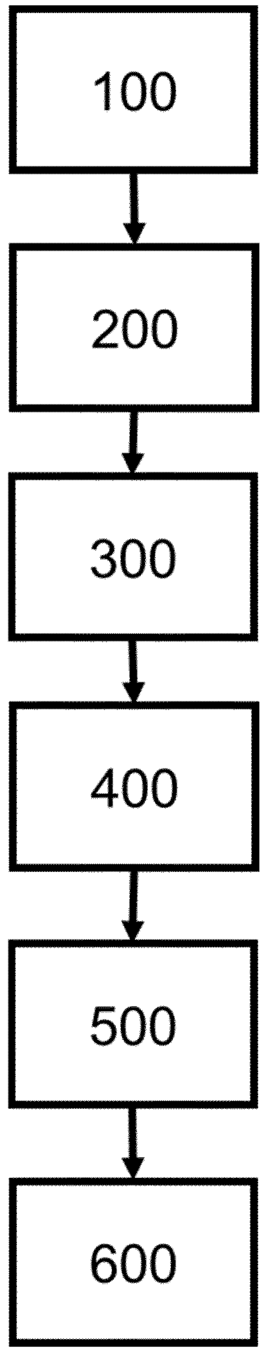
FIG. 1 is a flowchart of the workflow for planning an osteotomy.

FIG. 1 is a flowchart representing the main steps of the workflow allowing planning the osteotomy. Unless specifically stated, the steps may be carried out in a different order than the order presented in FIG. 1.

In step 100, an at least partial 3D model of the tibia and the femur is obtained.

If the tibia is to but cut, an at least partial model of fibula may also be necessary.

By "at least partial" is meant in the present text that a model of the whole tibia and femur may not be necessary, but only a model of these bones in the vicinity of the ankle, knee and/or hip (in particular to define the ankle, knee and hip centers), and in the region to be cut during the osteotomy procedure.

The requirement regarding the at least partial model(s) depends on the type of osteotomy to be performed, in particular on the location of the cut relative to the tibia and the femur.

Figure 2:
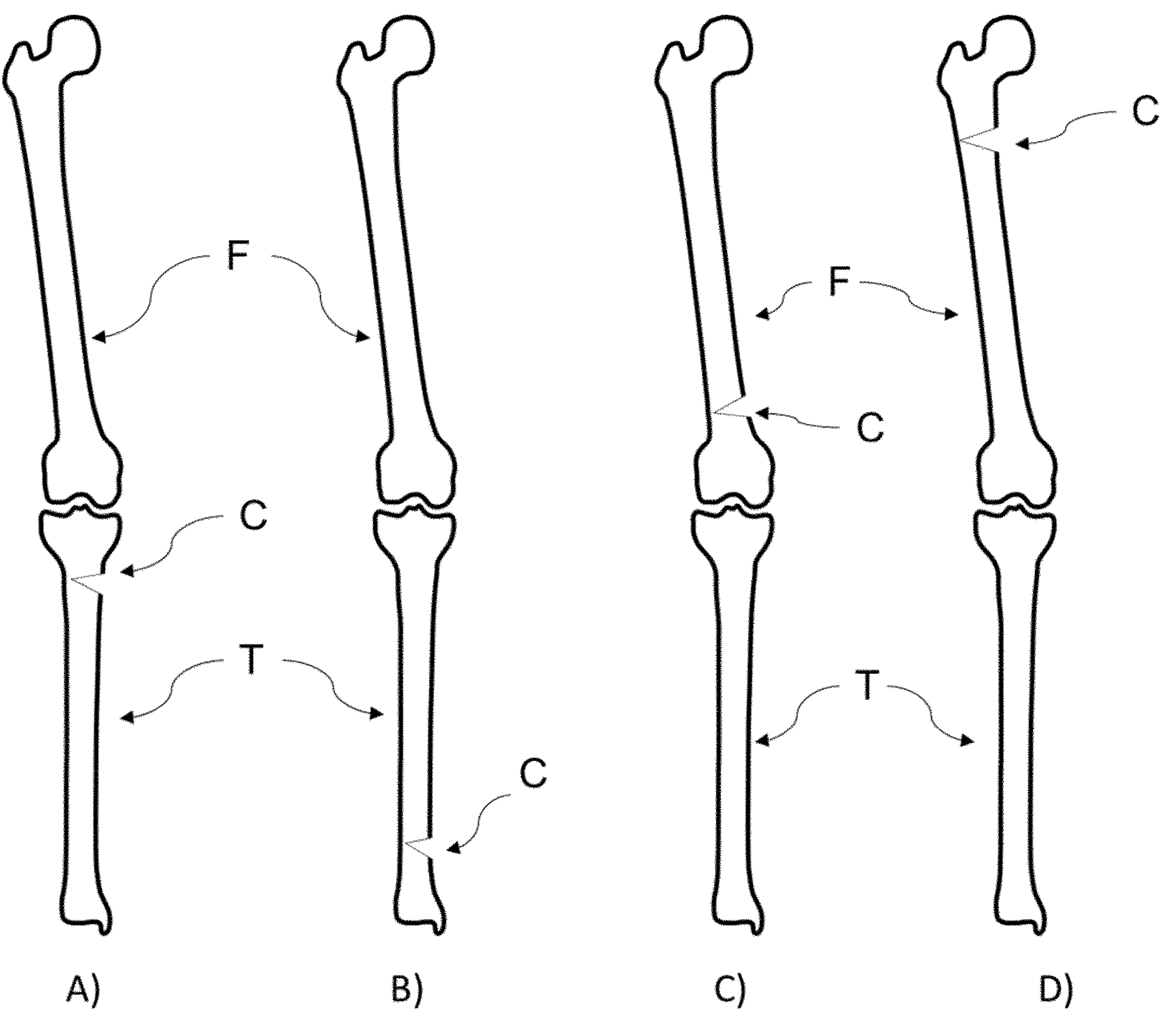
FIG. 2 schematically illustrates various cases of lower limb osteotomy.

FIG. 2 schematically illustrates various cases of lower limb osteotomy, in which the osteotomy cut is schematically represented under reference C.

A) high tibial osteotomy: at least a partial 3D model of the femur F and the tibia T is required;

B) distal tibial osteotomy: a least a partial 3D model of the tibia T is required;

C) distal femoral osteotomy: at least a partial 3D model of the femur F and the tibia T is required D) proximal femoral osteotomy: at least a partial 3D model of the femur F is required.

If several partial models are used, they have to be defined in a common coordinate system.

Such at least partial 3D models can be obtained by various methods known by the skilled person. For example, such bone models can be computed by automatic, semi-automatic or manual segmentation of a 3D medical image of the patient's leg or of portions of the patient's leg. Alternatively, the bone models can be obtained by palpation of the patient's bone. Alternatively, the models can be computed based on a standard model of the bone including characteristic points by adjusting said standard bone model to at least one 2D or 3D medical image of the patient's bone to match the patient's characteristic points. Of course, these techniques are not limitative and can be combined if appropriate. For example, segmentation may be assisted by bone surface palpation.

An advantage of working with 3D models is that they allow assessing multiple-plane deformities in three dimensions, which is hardly feasible with conventional 2D planning approaches.

The computation of the at least partial models may not be part of the present planning method, but may be considered as an input of the planning method, regardless of the technique used to obtain them.

In some embodiments, the at least partial 3D model of each bone can include only an outer surface of the bone, the bone being considered as a rigid uniform volume.

In more advanced embodiments, the at least partial 3D model of the bone can also include a biomechanical model of the bone, which takes into account non-uniformities in the bone structure and/or the influence of soft tissues. For example, a biomechanical model of the bone can include not only the outer surface of the bone but also several regions having different mechanical properties, such as cancellous bone regions and cortical bone regions, that do not deform the same way. A biomechanical model can also include the mechanical tension applied by ligaments or other soft tissues onto the bone, and/or conversely the mechanical tension applied by the bone onto soft tissues.

Such additional biomechanical information improves the accuracy of the simulation.

In step 200, a 3D model of the implant is obtained. This model includes the outer surface of the implant and also the through holes provided for screwing the implant into the bone.

Generally, such a 3D model is provided by the supplier of the implant. It may be available in a database of implant models.

The implant is selected by the surgeon in particular based on the type of osteotomy, and on the size and position of the wedge.

In step 300, a user (the surgeon or another member of the medical staff) enters at least one input comprising at least one target alignment parameter.

Said target alignment parameter(s) can be defined in a preoperative step, i.e. a step in which the patient is in a standing position, and/or in a preoperative step, i.e. in which the patient is in a lying position in the operating room. The intra-operative step is not limited to the surgical gesture itself but also includes the determination of the surgical plan.

Various target alignment parameters may be used and may be selected by the surgeon depending on the specific condition of the patient.

For example, but not limitatively, the target alignment parameter(s) may be:

- a mechanical femorotibial angle (mFTA),
- a mechanical medial proximal tibial angle (mMPTA),
- a mechanical lateral distal femoral angle (mLDFA),
- a lateral tibial plateau inclination (LTPI),
- a medial tibial plateau inclination (MTPI),
- a hip-knee-ankle angle (HKA): angle between the mechanical axes of the femur and the tibia,
- a joint line convergence angle (JLCA): angle made by a tangential line between the femoral condyles and the tibial plateau,
- a posterior tibial slope (PTS),
- a hip abduction angle (HAA),
- a tibial plafond inclination (TPI),
- a talar inclination angle (TIA),
- a lateral patellar tilt (LPT), and/or
- a lateral patellar shift (LPS).

Such target alignment parameters are determined relative to a set of anatomical landmarks (characteristic points).

Various methods for determining said set of characteristic points may be used.

In some embodiments, the characteristic points may be acquired by palpation using a pointer carrying a tracker tracked by a localization system, relative to trackers carried by the tibia and the femur in view of the implementation of the surgical procedure. In such a way, the position of each palpated point relative to at least one of the tibial and femoral trackers can be determined.

Figure 3:
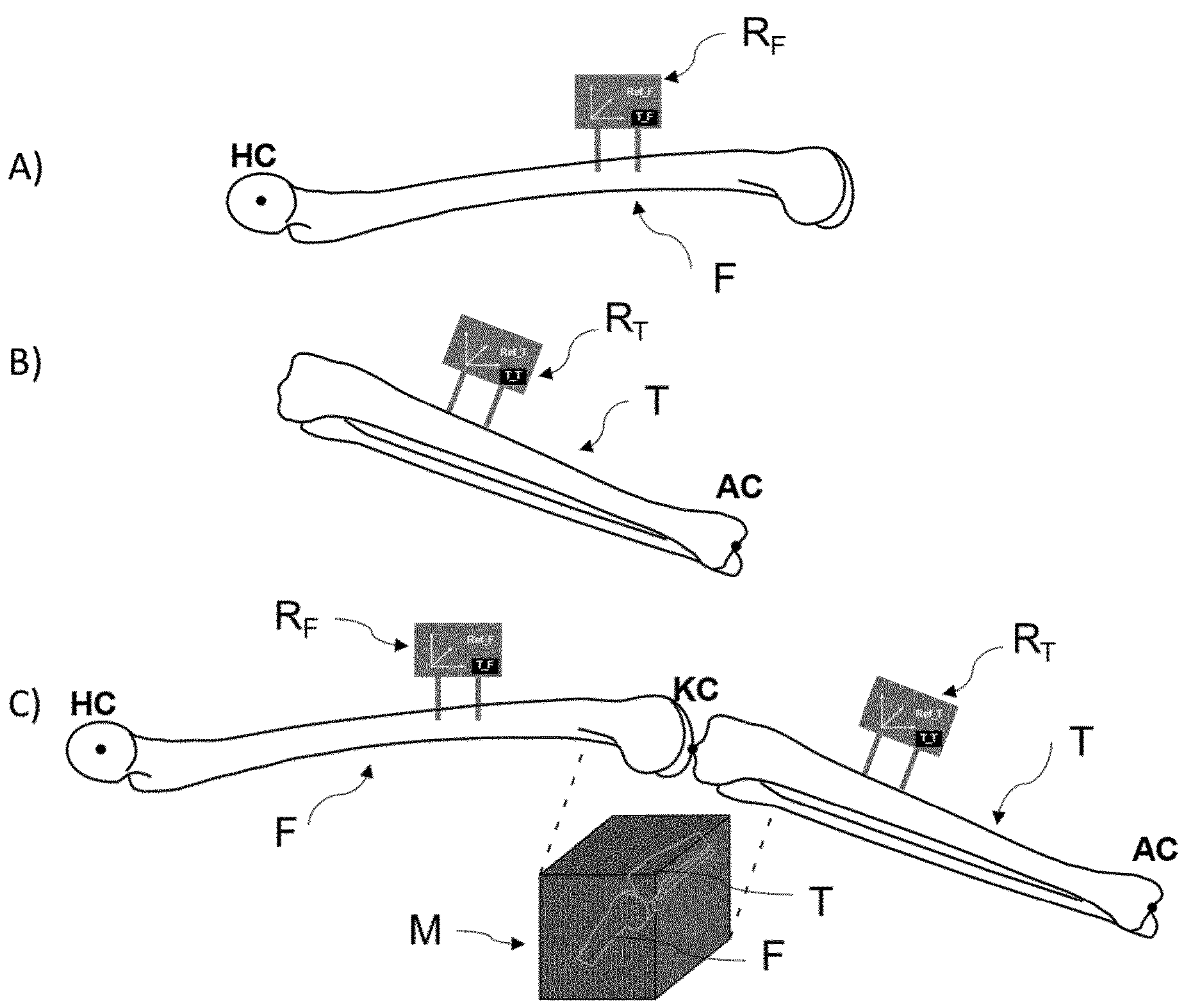
FIG. 3 schematically illustrates the determination of characteristic points of the bones.

As shown in FIG. 3, part A), characteristic points located on the femur bone F, for instance the hip center HC, are determined and located relative to a navigation tracker RF rigidly fixed on the femur bone. In part B) characteristic points located on the tibia bone T, for instance the ankle center AC, are determined and located relative to a navigation tracker RT rigidly fixed on the tibia bone. In part C), around the osteotomy region in case of high tibial osteotomy or distal femoral osteotomy, a partial 3D model M of the tibia T and the femur F is obtained. This model may be obtained for instance from an X-ray 3D imaging acquisition. Characteristic points on this 3D model, for instance the knee center KC, are determined and located relative to a navigation tracker rigidly fixed on the tibia bone and/or on the femur bone.

In other embodiments, the characteristic points may be determined on at least one 2D (bi-dimensional) or 3D (three-dimensional) X-ray image whose position in the coordinate system of at least one tracker is known. Preferably, said 2D or 3D X-ray image is acquired in the intra-operative step. Alternatively, the 2D or 3D X-ray image can be acquired pre-operatively. In such case, a registration is done between the pre-operative 2D or 3D X-ray image and the coordinate system of at least one of the tibial and femoral trackers.

The characteristic points can be identified based on a segmentation of the 2D or 3D X-ray image(s). For instance, the knee joint center can be located in at least one 2D or 3D image of the knee, via the analysis of one or more characteristic point(s) found on the images. In particular, different characteristic points of the image can be used to define the knee center. For instance, the knee center can be the average of two or more points: the midpoint of the femoral condyles or the center of the soft tissue outline.

Alternatively, the characteristic points can be identified in the at least partial 3D model of the tibia and/or the femur defined in step 100. If several partial models are used, they are defined in a common coordinate system.

Otherwise, the characteristic points may be present on a model of the bone and said model may be adjusted to the patient's bone using known bone morphing techniques, so as to register the characteristic points with a 2D or 3D X-ray image of the patient's bone.

Some characteristic points (for example, the center of a joint) may also be determined by moving the limb or a part of the limb about a joint. For example, the knee joint center can be located by using a morpho-functional method using flexion-extension movements. In such a morpho-functional method, 3D positions and orientations of the femoral and tibial trackers are recorded during the motion by the navigation system. An average rotation axis representing the flexion/extension is estimated.

Said methods are known by the skilled person and will not be described in detail in the present text.

Of course, the above methods can be combined to determine the characteristic points. For example, the hip, knee or ankle center can be obtained via the morpho-functional method and be adjusted via the information of the position of other characteristic points on a 2D or 3D X-ray image. In other situations, a partial determination of the characteristic points based on an incomplete bone segmented medical image or an incomplete bone morphing can be supplemented by the palpation of other characteristic points with a tracked pointer.

The target alignment parameter(s) may be determined by various techniques.

In some embodiments, the target alignment parameters can be determined based on 2D X-ray images, by measurements of specific features representative of the alignment of the leg.

Said 2D X-ray images can be acquired pre-operatively. In such case, the patient is generally in standing position. The pre-operative step can thus allow diagnosing directly a misalignment of the patient's leg and consequently determining the target alignment parameter(s) to be achieved by the osteotomy procedure to provide a correct alignment of the leg.

Alternatively, said 2D X-ray images can be acquired intra-operatively. In such case, the patient is generally lying on the operating table. In order to take into account laxities and influence of soft tissues, the surgeon applies mechanical constraints to the leg in order to achieve an alignment similar to the alignment that would be observed in the standing position. The surgeon uses his/her professional expertise and knowledge of patients' anatomy to apply suitable mechanical constraints and thus simulate the alignment in the standing position. As mentioned for the pre-operative step, the surgeon can then determine the target alignment parameter(s) to be achieved by the osteotomy procedure to provide a correct alignment of the leg.

Due to the length of the leg, it may not be possible or suitable to obtain a single X-ray image of the whole leg. Thus, several images of different parts of the leg can be acquired and recorded to allow determining target alignments of the leg.

However, the use of X-ray images is not compulsory to determine the target alignment parameters in the intra-operative step. For example, the navigation system alone can be sufficient to determine the relative positions of the femur and the tibia in all directions of a three-dimensional space, diagnose a misalignment of the leg and determine the target alignment parameter(s) to be achieved by the osteotomy procedure to provide a correct alignment of the leg. This allows reducing the patient's exposure to X-rays.

In addition to the target alignment parameter(s), the input entered in step 300 can also include:

- the type of surgical procedure,
- the type of osteotomy,
- at least one clinical parameter selected from: a hinge position, a zone not allowed to be cut, an entry point for the cut, and one or more cutting plane(s).

Alternatively, the input can be a validation of an automatic plan.

In step 400, a dynamic simulation of each cut is implemented.

By "dynamic" is meant in the present text that the simulation simulates not only the cut(s) made in each bone but also the movement of the bone portions to their final position defining the deformed position of the bone achieving the corrected alignment of the limb.

Said dynamic simulation is based on the at least partial 3D model of the tibia and the femur (and the fibula if appropriate).

The dynamic simulation can in particular include the computation of at least one cutting plane defining the two bone portions and at least one hinge zone to be preserved for each bone to be cut. Said computation can take into account predefined rules relating, for example, to a ratio between the cut and uncut areas. Such a ratio may be obtained from a plurality of experimental results, for example, from feedback relating to previous osteotomy procedures that lead to a fracture of the hinge zone.

The dynamic simulation can also comprise the computation of a displacement of the two bone portions relative to each other about the hinge zone until a final position to reach the at least one target alignment parameter.

If the at least partial 3D model of the bone is a biomechanical model, said computation can take in particular the type of bone in the hinge zone, or the influence of soft tissues, such as a tension exerted by the surrounding ligaments.

The dynamic simulation may be implemented by computing, for each phase of the displacement of the bone portions from their initial to their final position, a transformation matrix to be applied to the position of each point of the model of the bone to be cut at the beginning of said phase to determine the position of said point at the end of said phase. For example, if the movement of the bone portions from the initial to the final position is decomposed into N phases (N being an integer greater than or equal to 2), a transformation matrix $T_n$ is computed to represent the displacement (in translation and/or in rotation) of each point of the bone model in a phase n (n is an integer comprised between 1 and N, the position $P_0$ being considered as the initial position and the position $P_N$ being considered as the final position) from a position $P_{n-1}$ of said point at the end of the phase n−1 to a position $P_n$ of said point at the end of the phase n.

In some embodiments, the decomposition of the movement of the bone portions may be based on the determination of an arbitrary axis between positions $P_0$ and $P_N$. Depending on the type of model used for the bone, the decomposition of the movement along said arbitrary axis may vary. For example, if a rigid model of the bone is used, the global displacement may be decomposed in N identical elementary displacements along the arbitrary axis. If a biomechanical model is used, assuming that a same force is applied to the bone, an elementary displacement may be computed at each phase.

Other embodiments may rely on different methods for decomposing the movement of the bone portions and the present invention is not limited to a specific method.

During said simulated movement of the bone portions, the anatomical features (characteristic points) are monitored in real time in order to determine whether the current relative position of the bone portions allows reaching the target alignment parameter(s).

In the case of an open-wedge osteotomy, the relative movement of the bone portions is a distraction. In the case of a closed-wedge osteotomy, the movement is a closing of the bone portions.

As a result of this dynamic simulation, a deformed model of each bone to be cut resulting from the simulated cut(s) and movement, comprising the hinge zone and the two bone portions in the final position, is computed.

Regardless of the type of osteotomy (open-wedge or closed-wedge), the dynamic simulation can also compute the osteotomy wedge extending between the two bone portions in the final position.

Figure 4:
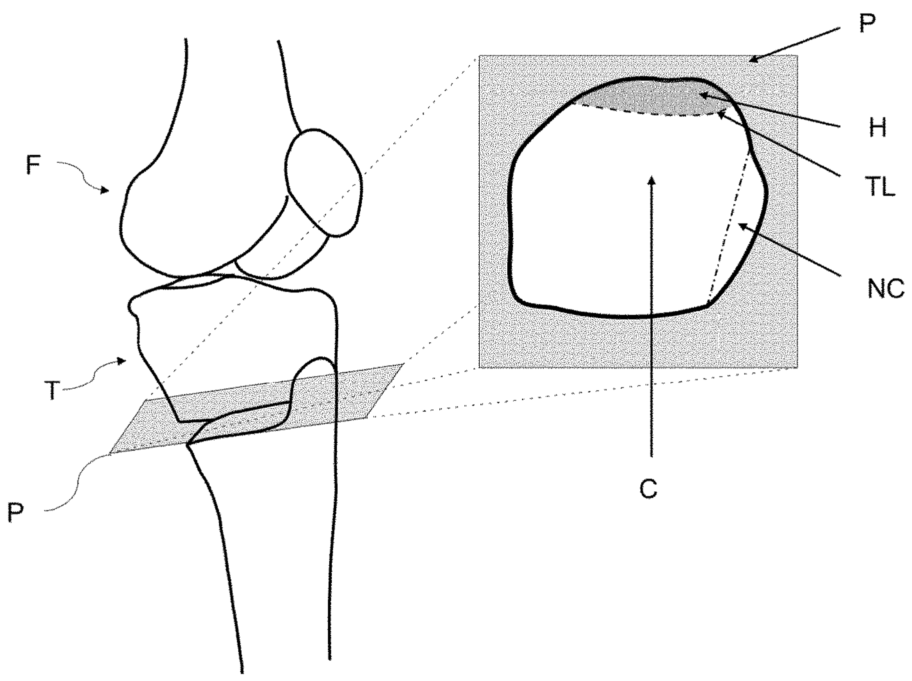
FIG. 4 schematically illustrates parameters of the osteotomy cut.

The computation of said osteotomy wedge can comprise the computation of the following parameters or combination of parameters (non-limitative list), as illustrated in FIG. 4:

- at least one osteotomy plane P according to which the bone is to be cut;
- a cut zone C, which is defined as an intersection between the at least partial 3D model M of the bone and said at least one osteotomy plane P;
- a no-cut zone NC, which is a zone of the bone along the osteotomy plane in which the bone must not be cut;
- a tilt line TL (which may be straight or curved), which is defined as a border of the cut zone about which the two bone portions are to be moved;
- the hinge zone H, which is defined as a zone on the at least one osteotomy plane in which no cut is carried out.

In some embodiments, the user can be requested to validate the computed wedge before the implementation of the subsequent steps of the planning method. The user can thus be allowed to modify the wedge if he is not satisfied by the computed wedge, in order that the optimal placement of the implant is computed based on the modified wedge.

Alternatively, such a validation may not be proposed to the user at the end of the dynamic simulation, but only at the end of the planning method, once the optimal placement of the implant has been computed.

An advantage of such a dynamic simulation is that it allows a multiple-objective optimization to achieve the target alignment parameter(s). Indeed, since the displacement of the bone portions from their initial to their final position is decomposed into small displacements, the optimization can be carried out on small elements, for example using the finite element method or other simulation methods based on more or less rough meshes of the bones.

In step 500, the optimal placement of the implant onto the deformed bone is computed based on the deformed bone model(s) obtained in step 400 and the 3D model of the implant.

Said optimal placement can be computed based on the following criteria, which may be combined:

- a protrusion of the implant from the bone surface is minimized;
- each screw hole of the implant is located in front of a bone surface;

the placement of the implant is carried out according to predetermined instructions of use;

screw orientation is optimised to maximise stress recovery—for example, if the implant allows some degrees of freedom in the screw orientation, the computation can take into these degrees of freedom to determine the optimal screw orientation to have the best stress recovery;

friction of the implant on surrounding soft tissues is minimized-if a biomechanical model of the bone is available.

This list is of course non-limitative. In particular, the computation can take into account any clinical knowledge that is relevant to make sure that the screw placement, size, orientation and the final tightening torque are not compromising the whole implant placement and the target alignment wanted by the surgeon.

As a result, the surgical plan comprises:

the implant placement on the cranial/caudal axis and on anterior/posterior axis;

the implant placement relative to the bone;

the placement of the implant on the lateral/medial axis, which is restraint by the bone and the implant design.

Depending on each implant design, there may exist other constraints to be taken into account in the method, such as the bending of the implant.

From the calculation of the implant placement, the position of the screw holes of the implant can also be computed.

Advantageously, an optimal size of the screws (among a plurality of available sizes), orientation and chronological order for fixing the implant to the bone portions through the screw holes is also computed. For example, a criterion to determine said optimal size and/or orientation of the screws can be the size of the hinge and bone portions. If the 3D model of the bone is a biomechanical model, a further criterion can be the type (e.g. cancellous/cortical bone) or mechanical properties of the bone portions in which the screws have to be placed. For example, the screw length can be selected to allow the screws to be bi-cortical.

In step 600, the deformed bone model and the implant are displayed.

The user can then validate the surgical plan, or correct it.

In particular, if the surgeon is not satisfied with the proposed deformation of the bone or placement of the implant, he may interactively modify the deformed bone model, the placement of the implant and/or the screws and/or any other parameter of the osteotomy procedure, such as the hinge zone, a cutting plane(s), an entry point, etc., within boundaries defined by physical constraints and best practice knowledge.

In some embodiments, if the surgeon modifies the deformed bone model, step 500 may be reiterated to compute the optimal placement of the implant based on the modified deformed bone model.

At each manual modification of the plan by the user, the characteristic points are tracked and the corresponding alignment parameters are adjusted accordingly.

Figure 5:
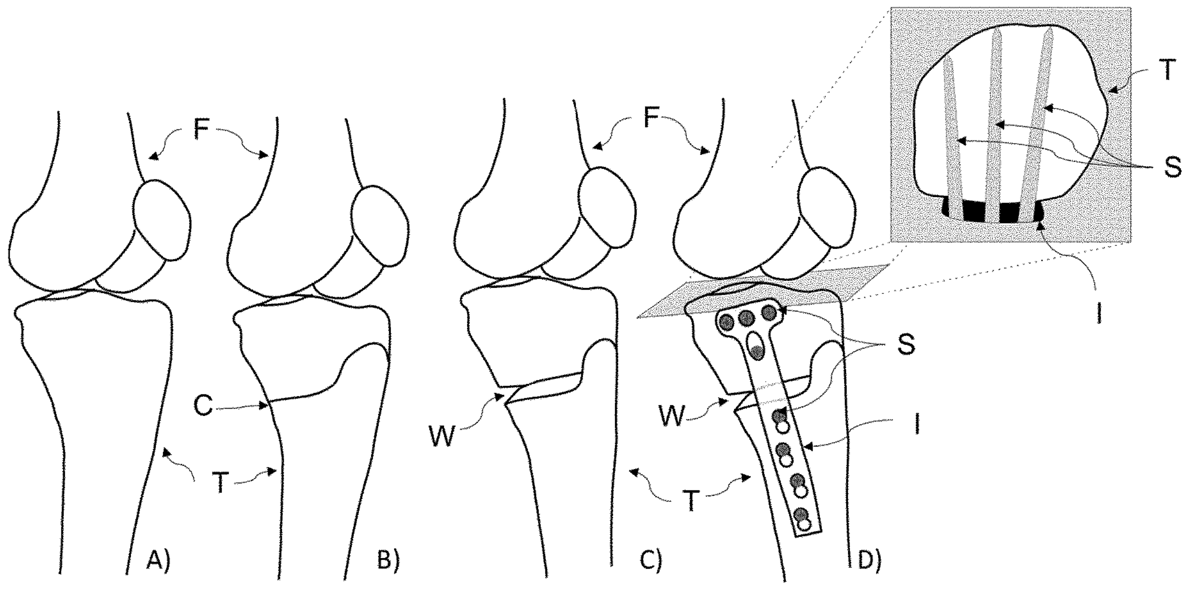
FIG. 5 schematically illustrates a model of the tibia and the femur during the main steps of the planning method of an open-wedge high tibial osteotomy.

FIG. 5 schematically illustrates a model of the tibia and the femur during the main steps of the planning method of an open-wedge high tibial osteotomy. Said model may be displayed at each step on the user interface.

Part A) shows the partial model of the tibia T and the femur F.

Part B) shows the cut C simulated on the partial model.

Part C) shows a simulated distraction of the portions of the tibia to form a wedge W.

Part D) shows the implant I and its screws S in an optimized position relative to the model, to maintain the wedge of part C) in a fixed position.

The displayed model may not be limited to a perspective view of the bone(s) but may also include one or several cross-sectional views, as shown in the inset in part D). Such a cross-sectional view allows visualizing the position of the screws with respect to the bone. If a biomechanical model of the bone is available showing the type of bone in the regions where the screws are to be implanted (e.g. cancellous/cortical bone), it can allow the user to check that the placement of the screws is optimal.

Once validated, the surgical plan can be used to carry out the surgical procedure.

In particular, the surgical plan can be implemented in a computer-assisted osteotomy procedure.

Figure 6:
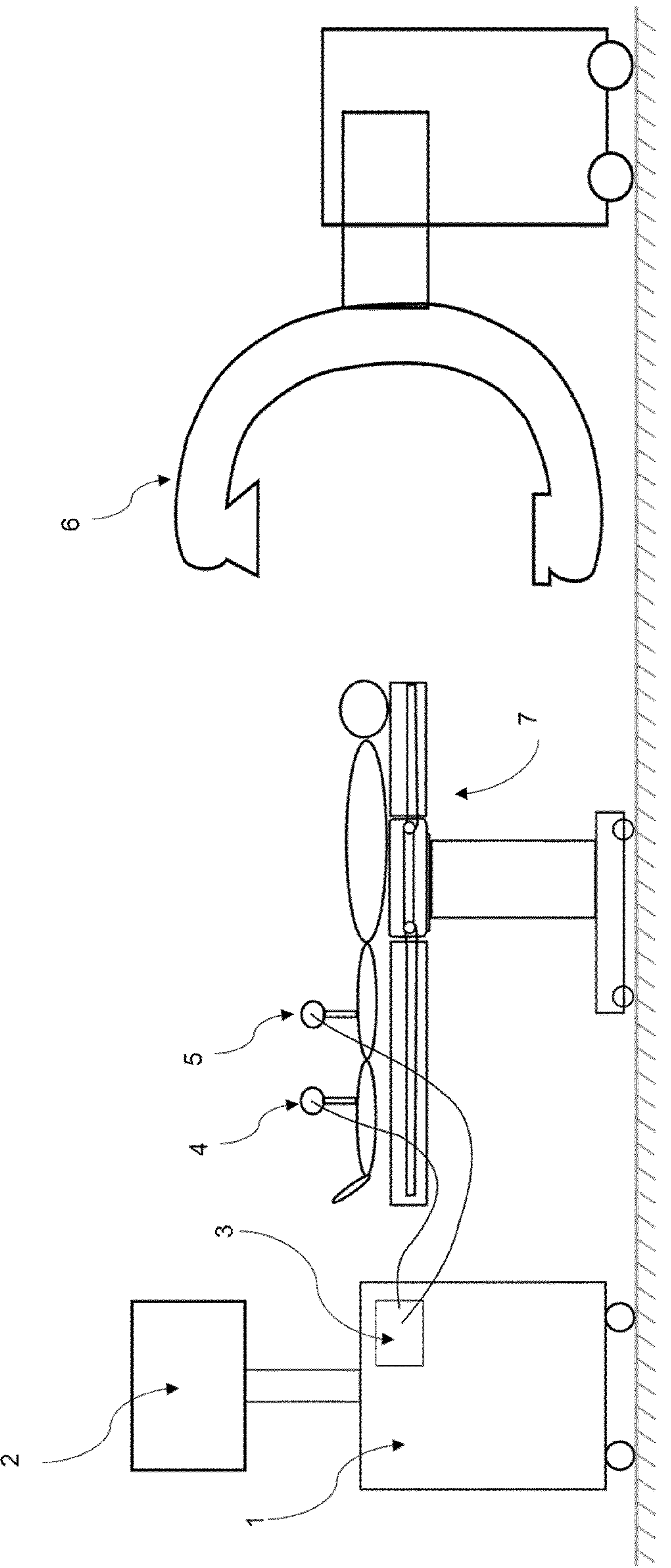
FIG. 6 illustrates a general overview of a surgical system allowing implementing the osteotomy.

For such a surgical procedure, the patient lies on an operating table 7 in an operating room, as shown in FIG. 6. A tibial tracker 4 is fixed to the patient's tibia and a femoral tracker 5 is fixed to the patient's femur, both trackers being tracked by a localization system.

Next to the operating table 7, a navigation station 1 comprises a control unit 3 and a display 2 for the user interface. In some embodiments, the display may be tactile.

Any localization technology may be used. In some embodiments, the localization system may include at least one camera and the trackers each comprise a respective set of markers with a unique geometry that can be detected by the camera. Said markers may be passive markers, such as disks or balls comprising a reflective surface adapted to reflect light from an infrared camera. Alternatively, the markers may be active markers that are themselves adapted to emit light, such as LEDs. In other embodiments, the localization system may include at least one electromagnetic emitter and receiver and the trackers may each comprise an electromagnetic receiver or emitter coupled to the localization system. In other embodiments, the localization system may comprise accelerometers, gyroscopes and/or magnetometers, in particular IMU (Inertial Measurement Unit) sensors.

The control unit is coupled to the localization system so as to receive localization data regarding the trackers.

For example, the tibial and femoral trackers 4, 5 are electromagnetic trackers and belong to an electromagnetic localization system. The trackers are linked to the control unit 3 to provide the control unit with localization data. If additional electromagnetic trackers are used, as explained below, they are also linked to the control unit.

In some embodiments, the surgical system also comprises a 2D and/or 3D intra-operative X-ray imaging system 6 that can be brought next to the patient to acquire 2D and/or 3D images. For example, the X-ray imaging system is a C-arm.

The localization system and the X-ray imaging system are known per se and will not be described in detail in the present text. In particular, localization systems and X-ray imaging systems currently available on the market can be used for carrying out the osteotomy procedure.

The trackers are tracked in real time by the localization system in order to determine the position and orientation of the tibia and the femur.

By "fixed" is meant a temporary (the tracker being intended to be removed after the surgical procedure) but rigid fixation of the tracker to the respective bone, so as to avoid any movement of the tracker relative to the bone during the surgical procedure. For example, each tracker may be implanted into the respective bone using a pin or a screw. A coordinate system is attached to each tracker and is thus tracked in real time by the localization system.

In addition, one additional tracker may be fixed to the bone to be cut, so that one tracker is fixed to a respective side of the osteotomy cut. Thanks to the additional tracker, the control unit can follow in real time the degree of opening or closing of the wedge formed by the osteotomy.

Figure 7:
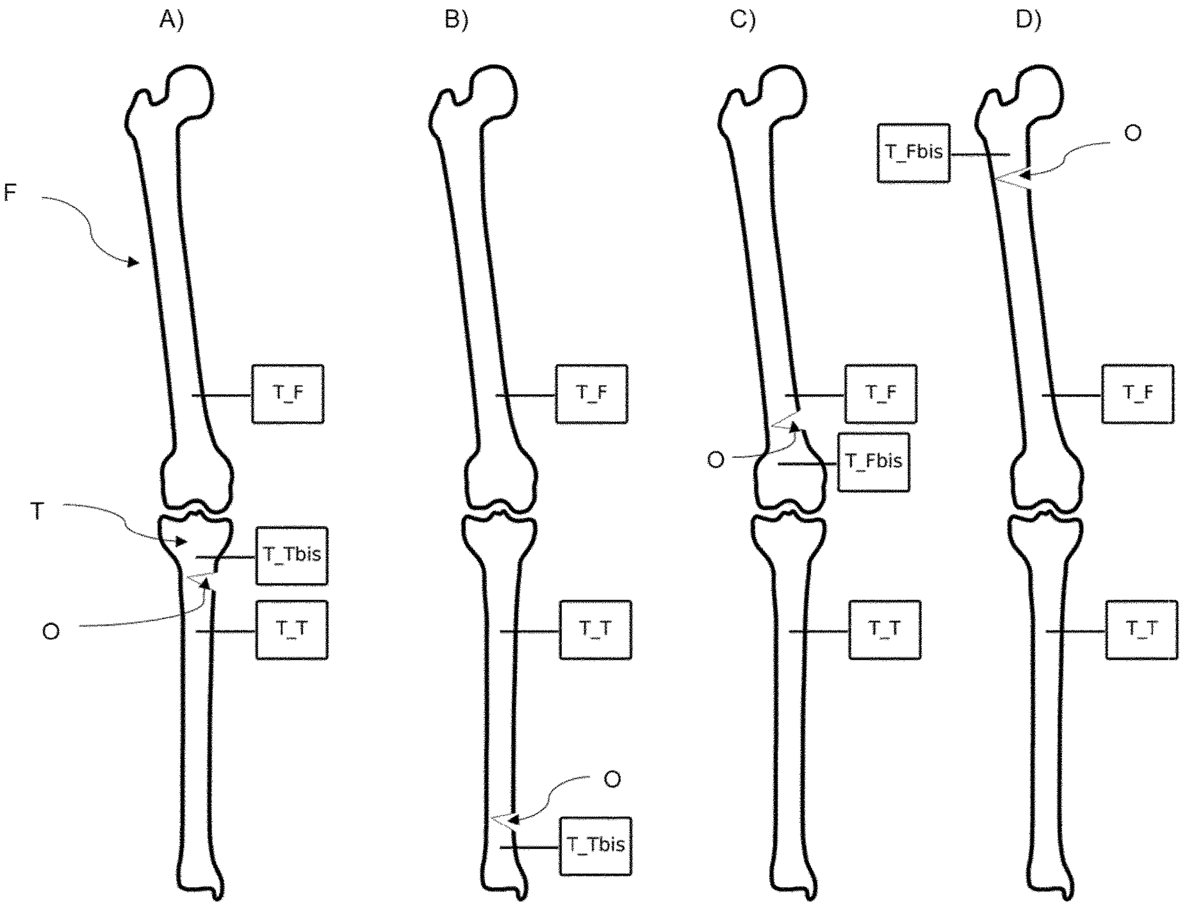
FIG. 7 schematically illustrates various embodiments of trackers placement for an osteotomy procedure.

FIG. 7 illustrates various embodiments of trackers placement.

In embodiment a), which corresponds to high tibial osteotomy, one tracker T_F is fixed to the femur F and two trackers T_T and T_Tbis are fixed to the tibia. The tracker T_Tbis is fixed to the upper part of the tibia, above the space O opened by osteotomy, and the tracker T_T is fixed to the lower part of the tibia, below the space O.

In embodiment b), which corresponds to distal tibial osteotomy, one tracker T_F is fixed to the femur F and two trackers T_T and T_Tbis are fixed to the tibia. The tracker T_Tbis is fixed to the lower part of the tibia, below the space O opened by osteotomy, and the tracker T_T is fixed to the upper part of the tibia, above the space O.

In embodiment c), which corresponds to distal femoral osteotomy, one tracker T_T is fixed to the tibia T and two trackers T_F and T_Fbis are fixed to the femur. The tracker T_Fbis is fixed to the lower part of the femur, below the space O opened by osteotomy, and the tracker T_F is fixed to the upper part of the femur, above the space O.

In embodiment d), which corresponds to high femoral osteotomy, one tracker T_T is fixed to the tibia T and two trackers T_F and T_Fbis are fixed to the femur. The tracker T_Fbis is fixed to the upper part of the femur, above the space O opened by osteotomy, and the tracker T_F is fixed to the lower part of the femur, below the space O.

These embodiments can be combined if appropriate, for example if an osteotomy cut has to be made on both the femur and the tibia (double level osteotomy).

However, other devices can be used to follow the advancement of the osteotomy, and the use of such an additional tracker T_Tbis and T_Fbis is thus optional. In such case, data from said device are also provided to the control unit in order to allow the control unit to follow in real time the degree of opening or closing of the wedge formed by the osteotomy.

In some embodiments, a mechanical device may be inserted within the cut, and be designed to expand or retract as the parts of the bone being cut are moved farther or closer to each other. Said mechanical device may include at least one sensor coupled to the control unit and configured to measure in real time an expansion or a retraction of the mechanical device.

Figure 8:
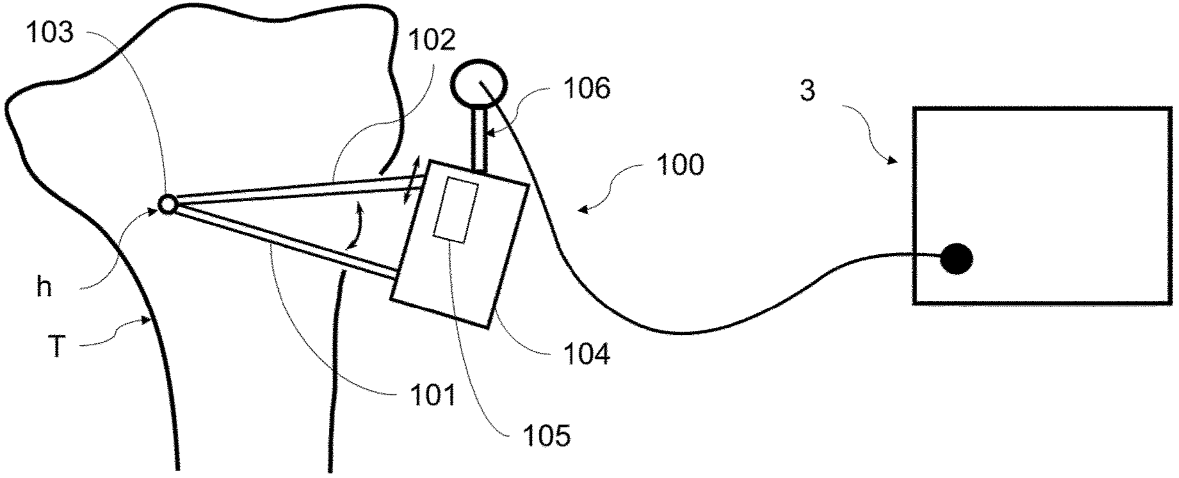
FIG. 8 schematically illustrates a mechanical device allowing monitoring the retraction or distraction of the bone.

FIG. 8 schematically illustrates an embodiment of such a medical device.

The mechanical device 100 comprises two plates 101, 102 connected to a mechanical hinge 103. The plates 101, 102 are coupled to a body 104. The plates are pivotable relative to each other about the mechanical hinge 103.

The angle between the two plates 101, 102 is precisely measured with an angle sensor 105 arranged in the body 104. The measurement data from the sensor 105 is sent to the control unit 3.

The mechanical device 100 further includes a tracker 106 belonging to the same localization system as the tibial and femoral trackers (that are not represented in FIG. 8 for sake of legibility of the figure). For example, the tracker 106 is an electromagnetic tracker and is linked to the control unit 3 in order to provide to the control unit localization data regarding the mechanical device 100 during its operation.

In case of closed-wedge osteotomy, the plates 101, 102 are inserted into the resected bone wedge so that the mechanical hinge 103 coincides with the bone hinge h, in order to monitor how the bone is retracted. Indeed, closing the wedge about the hinge h causes the plates 101, 102 to be moved toward each other, thereby decreasing the angle between the plates 101, 102, which is measured by the sensor 105.

In case of open-wedge osteotomy, the plates 101, 102 are inserted into the slot of the osteotomy bone cut, so that the mechanical hinge 103 coincides with the bone hinge h, in order to monitor how the bone is distracted. Indeed, distracting the bone parts about the hinge h causes the plates 101, 102 to be moved away from each other, thereby increasing the angle between the plates 101, 102, which is measured by the sensor 105.

Although illustrated in the tibia T in FIG. 8, the mechanical device 100 may be used in a similar way in case of femoral osteotomy.

In other embodiments, two mechanical devices may be fixed to both parts of the bone being cut, and linked by an adjustable link that is designed to expand or retract as the parts of the bone being cut are moved farther or closer to each other. Said link may include at least one sensor coupled to the control unit and configured to measure in real time an expansion or a retraction of the link.

Figure 9:
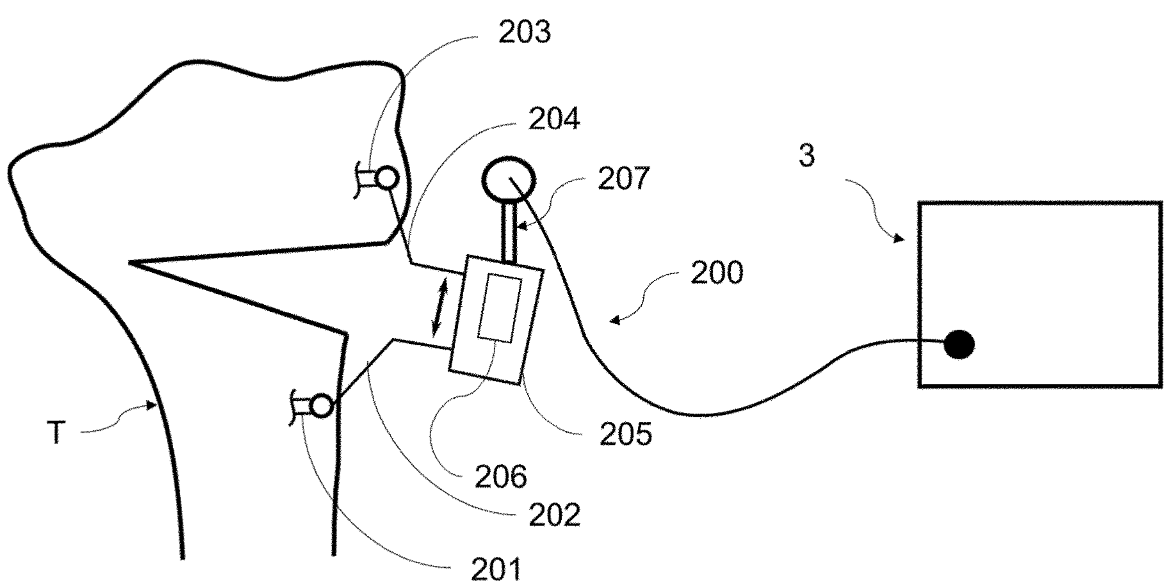
FIG. 9 schematically illustrates a mechanical assembly allowing monitoring the retraction or distraction of the bone.

FIG. 9 schematically illustrates an embodiment of such mechanical devices.

The mechanical assembly 200 comprises a body 205 and two plates 202, 204 connected to the body 205 by a hinge inside the main body.

Each plate 202, 204 is rigidly fixed to a respective part of the bone (e.g. the tibia T) around the osteotomy cut by a pin 201, 203 implanted into the bone.

The plates are movable relative to each other, thereby allowing moving the parts of the bone (and thus the pins 201, 203) closer or farther to each other about the hinge h.

The distance between the two pins 201, 203 is precisely measured with a displacement sensor 206 arranged in the body 205. The measurement data from the sensor 105 is sent to the control unit 3.

The mechanical assembly 200 further includes a tracker 207 belonging to the same localization system as the tibial and femoral trackers (that are not represented in FIG. 9 for sake of legibility of the figure). For example, the tracker 207 is an electromagnetic tracker and is linked to the control unit 3 in order to provide to the control unit localization data regarding the mechanical assembly 200 during its operation.

In case of closed-wedge osteotomy, the mechanical assembly is fixed below and above the resected bone wedge, so as to monitor how the bone is retracted.

In case of open-wedge osteotomy, the mechanical assembly is fixed below and above the slot of the osteotomy bone cut, so as to monitor how the bone is distracted.

The mechanical devices may be used in a similar way in case of femoral osteotomy.

Based on the surgical plan, the surgeon performs each planned cut so that at least one bone is partially divided in two portions articulated by a hinge.

Then, depending on the osteotomy type, the surgeon moves the bone portions away from each other (in particular in case of an open-wedge osteotomy) or toward each other (in particular in case of a closed-wedge osteotomy), until reaching the planned deformed configuration of the bone.

During said distraction or closing movement, the control unit receives localization data from the localization unit (and/or from any other device allowing tracking the advancement of the osteotomy) and is thus able to determine in real time the position of the bone portions.

Another advantage of the dynamic simulation is that it allows monitoring the osteotomy procedure and/or improve the biomechanical model.

In some embodiments, the control unit can be configured to compare in real time the current position of the bone portions with the theoretical position given by the dynamic simulation. As long as the result of said comparison is below a determined threshold, the control unit may assess a normal advancement of the osteotomy. If the result of said comparison exceeds said determined threshold, the control unit may assess that an incident has occurred, for example breakage of the hinge. In such case, the control unit may generate an alert to the surgeon as soon as the incident has been detected, e.g. via the user interface.

In some embodiments, the control unit may record the positions of the bone portions during the surgical intervention with a view of comparing it later with the theoretical positions given by the dynamic simulation. Based on the result of the surgical intervention (e.g. achieved correction, occurrence of incidents), the control unit may thus improve the biomechanical model. For example, if the final position of the bone portions obtained at the end of the osteotomy fits to the simulated position while the trajectory followed by the bone portions is different from the trajectory provided by the dynamic simulation, this difference can be used as new inputs of the impact of the soft tissues on the joint, to enrich the biomechanical model. To that end, the control unit may implement machine learning algorithms.

Since the position of the screws are determined with respect to the deformed bone model, it is also possible to determine the position of said screws in the initial configuration of the bone based on the surgical plan.

Thus, in the surgical procedure, the surgeon can advantageously drill the holes required for screw placement before implementing the osteotomy cut, or before distracting or closing the bone portions.

Said drilling can be assisted or implemented by a robotic arm holding or guiding a surgical drill.

Pins can be placed in the drill holes until final fixation of the implant. In particular, said pins can serve as guides for placing the implant once the bone portions have been distracted or closed according to the surgical plan.

The invention claimed is:

1. A computer-assisted method for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, comprising:

obtaining, at a processor of a computer, an at least partial 3D model of the tibia and/or the femur and a 3D model of the implant;

receiving, at the processor, at least one user input comprising at least one target alignment parameter;

based on the at least partial 3D model of each bone and the at least one user input, implementing by the processor a dynamic simulation of each cut and of distraction or closing of the bone portions to compute a deformed model of each bone to be cut resulting from the simulated cut(s) and distraction or closing taking into account predefined rules relating to a ratio between cut and uncut areas, said dynamic simulation comprising a simulation of the movement of the bone portions from an initial position prior to each bone cut to a final position defining the deformed configuration of the bone achieving a corrected alignment of the limb and preserving a hinge zone connecting the bone portions; and based on the deformed bone model(s) and the at least partial 3D model of the implant, computing by the processor an optimal placement of the implant onto the deformed bone.

2. The method of claim 1, wherein the dynamic simulation comprises:

computing by the processor at least one cutting plane defining the two bone portions and at least one hinge zone to be preserved for each bone to be cut;

computing by the processor a distraction or closing of the two bone portions relative to each other about the hinge zone until a final position to reach the at least one target alignment parameter;

computing by the processor the deformed bone model comprising the hinge zone and the two bone portions in said final position.

3. The method of claim 1, wherein the user input further comprises at least one of:

a type of surgery procedure, a type of osteotomy, a validation of an automatic plan, at least one clinical parameter selected from: a hinge position, a zone not allowed to be cut, an entry point for the cut, and a cutting plane.

4. The method of claim 1, wherein the at least one target alignment parameter comprises: a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA), a joint line convergence angle (JLCA), a posterior tibial slope (PTS), a hip abduction angle (HAA), a tibial plafond inclination (TPI), a talar inclination angle (TIA), a lateral patellar tilt (LPT) and/or a lateral patellar shift (LPS).

5. The method of claim 1, wherein the osteotomy procedure comprises an open-wedge osteotomy and the dynamic simulation of the cut and distraction of the bone portions computes an osteotomy wedge extending between the two bone portions.

6. The method of claim 1, wherein the osteotomy procedure comprises a closed-wedge osteotomy and the dynamic simulation of the cut and closing of the bone portions computes an osteotomy wedge extending between the two bone portions.

7. The method of claim 5, wherein the computation of said osteotomy wedge comprises the computation of at least one of:

at least one osteotomy plane according to which the bone is to be cut;

a cut zone defined as an intersection between the 3D model of the bone and said at least one osteotomy plane;

a tilt line defined as a border of the cut zone about which the two bone portions are to be distracted or closed; and the hinge zone being defined as a zone on the at least one osteotomy plane in which no cut is carried out.

8. The method of claim 5, comprising validating the osteotomy wedge by the user before computing the optimal placement of the implant.

9. The method of claim 1, further comprising identifying anatomical landmarks on the 3D model of the bone and taking into account said anatomical landmarks at the processor for implementing the dynamic simulation of the cut and the distraction or closing of the bone portions.

10. The method of claim 1, wherein the at least partial 3D model of the bone is a biomechanical model and wherein the dynamic simulation and the computation of the optimal placement of the implant are based on said biomechanical model so as to take into account influence of soft tissues onto the deformed bone.

11. The method of claim 1, wherein the optimal placement of the implant is computed based on at least one of the following constraints:

a protrusion of the implant from the bone surface is minimized;

each screw hole of the implant is located in front of a bone surface;

the placement of the implant is carried out according to predetermined instructions of use;

screw orientation is optimised to maximise stress recovery; and friction of the implant on surrounding soft tissues is minimized.

12. The method of claim 1, wherein the computation of the optimal placement of the implant comprises computing by the processor an optimal size and/or orientation of each screw for fixing the implant to the bone portions.

13. The method of claim 1, further comprising displaying the deformed bone model and the 3D model of the implant on a user interface.

14. The method of claim 1, wherein the at least partial 3D model of each bone is obtained by at least one of the following methods:

segmentation of a 3D image of the respective bone;

palpation of a surface of the respective bone; and bone morphing.

15. The method of claim 1, further comprising interactively modifying by a user the deformed bone model and/or the placement of the implant.

16. A system for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, said system comprising at least one processor and at least one user interface coupled to the at least one processor, wherein the at least one processor is configured to:

obtain an at least partial 3D model of the tibia and the femur and a 3D model of the implant;

receive at least one user input via the user interface comprising at least one target alignment parameter;

based on the at least partial 3D model of each bone and the at least one user input, implement a dynamic simulation of each cut and of distraction or closing of the bone portions to compute a deformed model of each bone to be cut resulting from the simulated cut(s) and distraction or closing taking into account predefined rules relating to a ration between cut and uncut areas, said dynamic simulation comprising a simulation of the movement of the bone portions from an initial position prior to each bone cut to a final position defining the deformed configuration of the bone achieving a corrected alignment of the limb and preserving a hinge zone connecting the bone portions; and based on the deformed bone model(s) and the at least partial 3D model of the implant, compute an optimal placement of the implant onto the deformed bone.

17. A computer-assisted method for an osteotomy procedure on at least one bone selected from a tibia and a femur of a patient's lower limb to correct a misalignment of the lower limb, in which the bone is to be partially cut into two bone portions articulated by a hinge zone, wherein the bone portions are to be distracted or closed until a deformed configuration of the bone and an implant is to be screwed to said bone portions to maintain the bone in said deformed configuration, the method comprising:

implementing the method of claim 1 to determine an optimal placement of the implant onto the bone in the deformed configuration;

fixing at least two trackers to the tibia and the femur;

performing at least one cut to create the two bone portions articulated by the hinge;

moving the bone portions away or toward each other to reach the planned deformed configuration; and fixing the implant to the bone portions to maintain the bone in the deformed configuration, the method comprising, during movement of the bone portions, determining, by a control unit, a current position and orientation of the bone portions in real time based on localization data relating to the trackers, and comparing in real time said current positions and orientations with theoretical positions and orientations provided by the dynamic simulation.

18. The method of claim 17, further comprising fixing an additional tracker to the bone to be partially cut so that at least one tracker is fixed to each bone portion generated by the at least one cut.

19. The method of claim 17, further comprising coupling to the bone to be cut a mechanical device configured to expand or retract as the parts of the bone are moved farther or closer to each other, the mechanical device including at least one sensor coupled to the control unit and configured to measure in real time an expansion or a retraction of the mechanical device.

20. A computer-assisted method for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, comprising:

obtaining, at a processor of a computer, an at least partial 3D biomechanical model of the tibia and/or the femur and a 3D model of the implant;

receiving, at the processor, at least one user input comprising at least one target alignment parameter;

based on the at least partial 3D biomechanical model of each bone and the at least one user input, implementing by the processor a dynamic simulation of each cut and of distraction or closing of the bone portions to compute a deformed model of each bone to be cut resulting from the simulated cut(s) and distraction or closing, said dynamic simulation comprising a simulation of the movement of the bone portions from an initial position prior to each bone cut to a final position defining the deformed configuration of the bone achieving a corrected alignment of the limb; and based on the deformed bone model(s) and the at least partial 3D model of the implant, computing by the processor an optimal placement of the implant onto the deformed bone;

wherein the dynamic simulation and the computation of the optimal placement of the implant are based on the at least partial 3D biomechanical model so as to take into account influence of soft tissues onto the deformed bone.

21. A computer-assisted method for planning an osteotomy procedure on at least one bone selected from a tibia and a femur of a patient's lower limb to correct a misalignment of said lower limb, in which said bone is to be partially cut into two bone portions articulated by a hinge zone, said bone portions are to be distracted or closed until a deformed configuration of the bone and an implant is to be screwed to said bone portions to maintain the bone in said deformed configuration, comprising:

obtaining, at a processor of a computer, an at least partial 3D model of the tibia and/or the femur and a 3D model of the implant;

receiving, at the processor, at least one user input comprising at least one target alignment parameter;

based on the at least partial 3D model of each bone and the at least one user input, implementing by the processor a dynamic simulation of each cut and of distraction or closing of the bone portions to compute a deformed model of each bone to be cut resulting from the simulated cut(s) and distraction or closing, said dynamic simulation comprising a simulation of the movement of the bone portions from an initial position prior to each bone cut to a final position defining the deformed configuration of the bone achieving a corrected alignment of the limb, the movement being decomposed into N phases, N being an integer greater than or equal to 2; and based on the deformed bone model(s) and the at least partial 3D model of the implant, computing by the processor an optimal placement of the implant onto the deformed bone;

wherein the dynamic simulation comprises, for each phase:

computing a transformation matrix to be applied to the position of each point of the at least partial 3D model of the bone to be cut at the beginning of said phase to determine the position of said point at the end of said phase;

monitoring anatomical features to determine whether a relative position of the bone portions at the end of said phase allows reaching the at least one target alignment parameter.

* * * * *